(12) United States Patent
Stasey et al.

(10) Patent No.: US 10,188,152 B2
(45) Date of Patent: Jan. 29, 2019

(54) SYSTEM FOR MINIMIZING MULTI-DIMENSIONAL BREAST DISPLACEMENT

(71) Applicant: Recovery Force, LLC, Fishers, IN (US)

(72) Inventors: Brian J. Stasey, Fishers, IN (US); Mark Gummin, Silverton, OR (US); Matthew W. Wyatt, Fishers, IN (US)

(73) Assignee: Recovery Force, LLC, Fishers, IN (US)

( * ) Notice: Subject to any disclaimer, the term of this patent is extended or adjusted under 35 U.S.C. 154(b) by 141 days.

(21) Appl. No.: 15/410,551

(22) Filed: Jan. 19, 2017

(65) Prior Publication Data

US 2017/0202271 A1 Jul. 20, 2017

Related U.S. Application Data

(60) Provisional application No. 62/280,165, filed on Jan. 19, 2016.

(51) Int. Cl.
| | |
|---|---|
| *A41C 3/00* | (2006.01) |
| *A41C 3/12* | (2006.01) |
| *A61B 5/11* | (2006.01) |
| *A61B 5/00* | (2006.01) |

(52) U.S. Cl.
CPC ........... *A41C 3/0057* (2013.01); *A41C 3/12* (2013.01); *A61B 5/11* (2013.01); *A61B 5/4312* (2013.01); *A61B 5/6804* (2013.01); *A61B 5/6823* (2013.01); *A61B 2562/0219* (2013.01)

(58) Field of Classification Search
CPC ........... A41C 3/0057; A41C 3/12; A61B 5/11; A61B 5/4312; A61B 5/6804; A61B 5/6823
USPC ............................................... 450/41, 45, 86
See application file for complete search history.

(56) References Cited

U.S. PATENT DOCUMENTS

| | | | |
|---|---|---|---|
| 9,131,892 B2 * | 9/2015 | Markel | A61B 5/0015 |
| 2008/0287770 A1 * | 11/2008 | Kurzweil | A61B 5/0408 600/388 |
| 2009/0088652 A1 * | 4/2009 | Tremblay | A41D 13/1281 600/388 |
| 2017/0172502 A1 * | 6/2017 | Rofe | A41C 3/04 |
| 2017/0202271 A1 * | 7/2017 | Stasey | A41C 3/0057 |
| 2017/0202276 A1 * | 7/2017 | Wyatt | A41C 1/12 |

* cited by examiner

*Primary Examiner* — Gloria Hale
(74) *Attorney, Agent, or Firm* — Maginot, Moore & Beck, LLP

(57) ABSTRACT

A bra incorporates shape memory alloy, either in shape memory or super-elastic states, an accelerometer, a power source, a microprocessor, and an algorithm implemented by the microprocessor to learn and adapt to the displacement pattern of the wearer's breast during a physical activity. The shape memory alloy is in the form of SMA or super-elastic wires integrated into portions of the bra, whereby activating the wire(s) shortens the corresponding wire to produce a compressive force on the breast within the bra. The system thereby provides real-time, active suspension to control breast displacement or bounce. The system provides real-time feedback to a memory or super-elastic material integrated into the bra to provide adaptive force and displacement to counteract the push-off and landing forces at each footfall of the moving wearer affecting breast displacement.

15 Claims, 3 Drawing Sheets

SYSTEM FOR MINIMIZING MULTI-DIMENSIONAL BREAST DISPLACEMENT

PRIORITY CLAIM

This application is a utility filing from and claims priority to provisional application No. 62/280,165, filed on Jan. 19, 2016. The entire disclosure of this provisional application is incorporated herein by reference.

BACKGROUND

Women athletes typically desire a bra that meets three requirements. First and foremost, the bra must control movement of the breasts. Second, the bra needs to be comfortable, even during strenuous physical activity. A third requirement is often that the bra should maintain a certain visual aesthetic. Most female athletes have to settle for one or two of these requirements. There is currently no solution that provides all three requirements in one bra. If the bra provides excellent control of movement, it is usually not comfortable and generally presents an undesirable appearance because of the way the bra flattens the breasts and compresses the chest cavity. If the bra is comfortable it generally cannot provide enough compression to control the breasts during aggressive athletic motions. Bra that provide natural shaping and movement, can often be comfortable but at the cost of providing the necessary control.

There is a significant need for a bra, or "sports" bra, that meets all of these requirements.

SUMMARY OF THE DISCLOSURE

The system disclosed herein incorporates shape memory alloy, either in shape memory or super-elastic states, an accelerometer, a power source, a microprocessor, and an algorithm implemented by the microprocessor to learn and adapt to the displacement pattern of the wearer's breast during a physical activity. The system thereby provides real-time, active suspension to control breast displacement or bounce. The system provides real-time feedback to a shape memory or super-elastic material integrated into the bra to provide adaptive force and displacement to counteract the push-off and landing forces at each footfall of the moving wearer affecting breast displacement.

DETAILED DESCRIPTION

Figure 1:
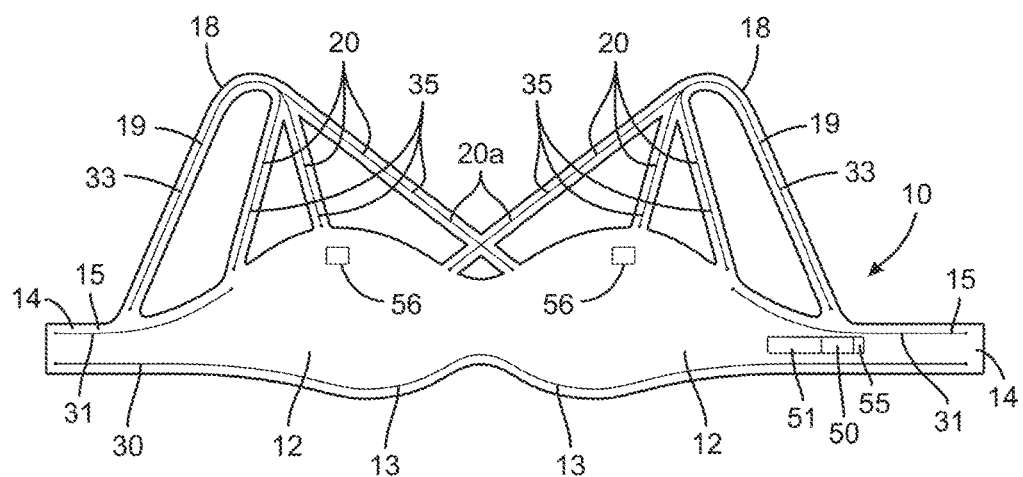
FIG. 1 is a front view of a bra according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains Existing compression bras are very tight all the time, flattening the breasts and making it difficult to expand the chest cavity to take a full deep breath. The bra of the present disclosure provides a gentle compression for maximum comfort under generally static conditions, while still providing necessary support under dynamic loading. In one implementation, memory materials elements are integrated into structure of the bra. Memory material elements in the straps of the bra are configured to exhibit a longer (comfortable) length in the generally static conditions and a shorter (compressive) length in dynamic loading conditions. In most situations, the memory material elements in the straps are not energized and are maintained in their natural state which is the longer length. When motion above a certain athletic threshold is detected by an accelerometer, the memory material is energized in such a way that it shrinks to the shorter (compressive) length. The materials are kept at the shorter (compressive) length until such time that dynamic activity stops for a set amount of time, at which time the memory material is de-energized and returns to its longer (comfortable) length.

The present disclosure contemplates the integration of wires formed of shape memory alloys, either as shape memory components or super-elastic components. For the purposes of the present disclosure the term "shape memory alloy" refers to alloys, such as nickel titanium, that undergo a phase transformation in their crystal structure when cooled from the stronger, high temperature form (Austenite) to the weaker, low temperature form (Martensite) to include alloys capable of shape memory and super-elasticity.

When a shape memory alloy is in its Martensitic form, it is easily deformed to a new shape. However, when the alloy is heated through its transformation temperatures, it reverts to austenite and recovers its previous shape in a process known as shape memory. The temperature at which the alloy remembers its high temperature form when heated can be adjusted by slight changes in alloy composition and through heat treatment. In the Nickel Titanium alloys, for instance, it can be changed from above +100 deg.C to below −100 deg.C. The shape recovery process occurs over a range of just a few degrees and the start or finish of the transformation can be controlled to within a degree or two if necessary. Alloys used only for their shape memory characteristics in the embodiments disclosed herein are referred to herein as SMA materials.

Alloys used for their super-elasticity in the embodiments disclosed herein are referred to as super-elastic. These unique alloys also show a super-elastic behavior if deformed at a temperature which is slightly above their transformation temperatures. This effect is caused by the stress-induced formation of some Martensite above its normal temperature. Because it has been formed above its normal temperature, the Martensite reverts immediately to undeformed austenite as soon as the stress is removed. This process provides a very springy, "rubberlike" elasticity in these alloys.

In accordance with the present disclosure, these shape memory alloys are used in wires—either SMA wires or super-elastic wires—and the temperature changes are produced by ohmically heating the wires. The wires are thus connected to a power supply, by way of a controller that can control when current is applied to the wire—i.e., energize or activate the wire—and when the current is terminated to the wire—i.e., de-energize or de-activate the wire.

A bra according to the present disclosure is illustrated in FIG. 1. The bra 10 can be of standard construction with a pair of cups 12 for receiving the breasts and laterally extending straps 14 adapted to encircle the torso of the woman. The torso straps may be individual straps with conventional fasteners at the ends of the straps for connecting the straps, or may be continuous as in typical sports bras. The continuous torso straps rely on elasticity to allow the woman to put the bra on; however, this same elasticity provides significant compression of the chest cavity. While the system disclosed herein can be incorporated into the continuous torso strap bra it is less desirable due to the compression characteristics inherent with such bras.

The bra 10 further includes a pair of upper strap arrangements 18 extending from the upper edge of the cups 12 and torso straps 14. The strap arrangement 18 includes shoulder straps 19 configured to seat on the shoulders of the woman in a known manner. The strap arrangements further include a number of forward straps 20 that extend from the upper edge of the cups 12 and spaced across the upper edge to provide uniform support forces. The two center straps 20a may criss-cross at the center of the bra, as depicted in FIG. 1.

In one feature of the present disclosure, shape memory material elements are integrated into the structure of the bra. In particular, the shape memory material elements include wires formed of a shape memory alloy (SMA) material that is activated by the application of electrical current. In one specific embodiment, the wires may be Nitinol wires. In one embodiment, an SMA wire 30 extends across the underwire region 13 of the bra cups and across the lower edge of the torso straps 14. It has been found that compression at this location has less of an impact on Vo2 (volume of oxygen lungs can uptake) and comfort of the woman athlete. SMA wire attached to the underwire of the bra pushes the breasts up as it shrinks, providing additional support. Additional SMA wires 31 may be integrated into the upper edge 15 of the torso straps for further stability during movement. SMA wires 33 and 35 are integrated into the strap array 18, with wires 33 integrated into the shoulder straps 19 and SMA wires 35 integrated into the central straps 20, each configured to provide compression at the upper section of the bra to flatten the breasts into the body. The SMA wires 35 in the central straps 20 converge to a common point on the back of the wearer but provide three distributed attachment points around the top of each cup 12. This arrangement of straps and SMA wires provides different points around the breasts to grain supportive leverage or compression to control breast movements when the SMA wires are activated.

A Nitinol SMA wire having a transition temperature ($A_S$) of 105° F. will react quickly to Joule heating. The SMA wires will contract 4%-5% (of its total length) in less than two seconds when heated ohmically at about 12 Volts. The Nitinol material with a 105° F. transition temperature requires a lesser amount of heat energy to transition the wire to its shorter (compressive) length compared to other SMA's such as Dynalloy LT or HT. The lower transition temperature Nitinol wire also uses about 20% less power than Dynalloy LT to achieve its maximum shortening of length. Thus, low temperature Nitinol is a preferred SMA for incorporation into a bra that is intended to be worn. However, other SMA wires may be used, including the Dynalloy wires, with appropriate insulation to protect the wearer from potentially excessive heat.

In one example, the Nitinol wires 30, 31, 33 and 35 can have a diameter of 0.006". The wires can have a length of about 16" so that the nominal shortening of any wire will be 0.6-0.8 inches. This amount of shortening is sufficient to apply compression to the breast without over-compressing the torso of the wearer.

Figure 2:
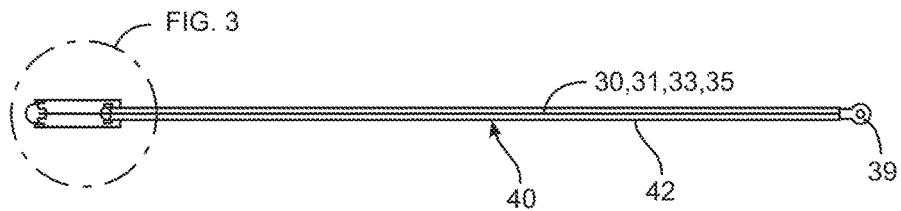
FIG. 2 is a side view of an SMA or super-elastic wire for use in the bra of FIG. 1.

Each SMA wire may be part of a wire assembly 40 as shown in FIG. 2. The SMA or Nitinol wire 30, 31, 33, 35 is mounted in a protective tube 42. The protective tube is formed of a flexible material that is preferably at least somewhat thermally insulating. The protective tube 42 protects the enclosed wire 30, 31, 33, 35 from the fabric of the bra and from moisture (such as sweat) absorbed by the bra during the activity. The protective tube has a length calibrated to extend over only a portion of the normal, non-activated length of the wire. In particular, the length of the tube 42 is less than the shortened, or activated, length of the wire. Thus, in the previous example, the shortened length of the wire is 15.2-15.4 inches, so the tube 42 has a length of 15.0 inches.

Figure 3:
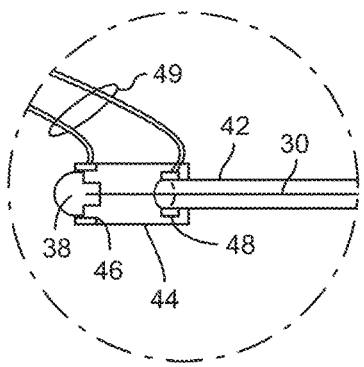
FIG. 3 is an enlarged view of one end of the SMA or super-elastic wire shown in FIG. 2.

The reduction in length of the SMA wire as it is activated is accommodated by the end construction of the wire assembly 40, shown in the enlarged view of FIG. 3. The end of the wire 30 shown in FIG. 3 is affixed to a cap 38 and the cap is itself affixed to a sliding tube 44. The opposite end of the wire is affixed to an electrical contact 39 which is itself affixed to the opposite end of the protective tube 42. The sliding tube 44 is sized to telescopingly engage the protective tube 42. When the wire 31 is activated, it's length decreases which draws the cap 38 toward the fixed contact 39 at the opposite end of the protective tube. The sliding tube slides over the protective tube so that the entire length of the wire 31 is enclosed. The sliding tube 44 and the protective tube 42 may include respective electrical contacts 46, 48 that are arranged to contact each other only when the wire has shrunk to its calibrated minimum length or has exceeded a predetermined force or stress.

The electrical contacts 46, 48 can be connected to a controller 50 mounted to the bra by wires 49. The controller 50 is operable to energize the SMA wires, as discussed herein, and to receive a signal from the contacts 46, 48 when they contact each other. Upon receipt of this signal, the controller 50 deactivates the corresponding SMA wire to ensure that the wire does not over-tighten. The SMA wire can be maintained in this optimum reduced length by using the contacts 46, 48 on the two tubes. When the controller 50 de-activates the wire it begins to return to its normal, non-energized length. As the wire lengthens, the electrical circuit formed by the two contacts 46, 48 is broken. When the controller 50 senses that the circuit is broken it re-energizes the wire, which causes the wire to shrink until again the contacts 46, 48 meet. With each re-energization, the activation of the wire requires significantly less electrical power than to initially energize the wire. This cycling feature allows the wire to be maintained in its shortened length with only minimal power from the controller 50. This provides a point where much less power is needed to hold the wire in the shrunk position. For instance, the shoulder strap 19 can be held in the compressed position with only four watts of power input to the SMA wire and with this power input the SMA wire can exert up to 1 lbf. Other methods of holding the wire at the shorter (compressive) length can be a strain gauge, where the wire is controlled via the amount of force it exerts on the gauge. With this approach, the wire is initially energized to 1 lbf, and then is cycled through deactivation if the strain gauge shows a force above 1 lbf, and re-activation if the strain gauge shows that force has dropped below the 1 lbf power threshold.

In the embodiment just described, the SMA wires are actuated to for active or calibrated tightening of the bra on the wearer. A typical sports bra works by being tight around the torso and breasts of the wearer. While this tightness can restrict breast movement, it tends to "flatten" the breasts and can be uncomfortable. With the SMA wire aspect of the bra of the present disclosure, the bra can be tightened in a calibrated manner, meaning that it is tightened where it is needed to reduce displacement and is only tightened as much as is necessary to optimize the displacement reduction. The controller includes a processor that can execute instructions to first determine whether a footfall has occurred based on data from the accelerometer 55 and then to obtain breast displacement data. The breast displacement data can be obtained from devices 56 in the cups 12 configured to measure displacement. If the displacement data is outside a threshold value the controller activates one or more of the SMA wires to tighten the bra about each breast. Since each breast will displace differently, each cup is tightened differently. At the next footfall, as indicated by the accelerometer 55, new displacement data is obtained from the devices 56 and the controller determines whether the displacement has been reduced to the desired threshold. If not, then the controller increases the activation of selected ones of the SMA wires. This process continues over a number of footfalls until the controller "learns" the pattern of movement of the wearer, at which point the controller continuously cycles the SMA wires according to the "learned" protocol to reduce breast displacement at every footfall. As the wearer's gait changes the controller 50 recognizes the change and "recalibrates" the actuation of the SMA wires until the breast movement is effectively reduced.

Elastic and memory material may provide independent suspension or may be combined in a way to provide a suspension similar to an automotive active suspension. Early suspension systems included suspension springs that are much like the straps in a conventional bra—they dampened the hardest shocks but did not prevent displacement. The suspension springs took the edge off of the shock but did not deal with the bouncing on the theory that it was better to oscillate than to jolt. The addition of a shock absorber to the vehicle suspension system dampened the effect of the rebound of the suspension spring, but again did not prevent the oscillation. Current active suspension systems correlate the application of a displacement resistant force to a shock load to minimize displacement and maximize comfort. While automotive suspension systems have evolved to active systems, the bra has not.

In addition to the calibrated tightening feature described above, the present invention contemplates placing an independent active suspension into a bra by integrating super-elastic Nitinol wires into the bra structure, and particularly into the upper strap arrangements 18. The super-elastic Nitinol wire acts as a damper as it is stretched within the strap due to athletic motion by the wearer. This dampening action can be further controlled by ohmically heating the wire so as to prevent the wire from further stretching and even providing a counter-force to shorten the wire back to its unstretched length.

Figure 4:
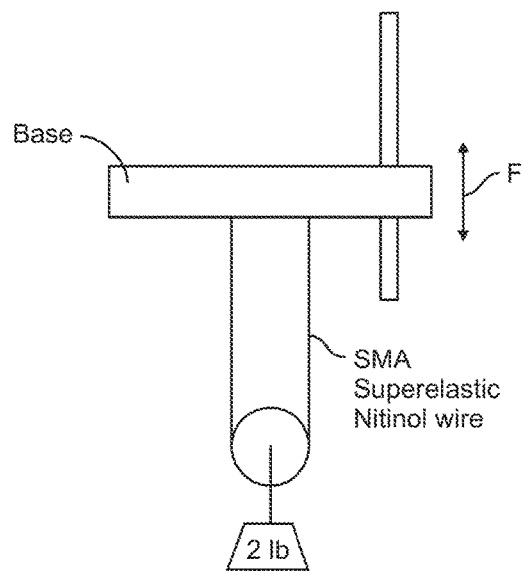
FIG. 4 is a schematic representation of the operation of the SMA or super-elastic wire and controller of the bra shown in FIG. 1.
Figure 5:
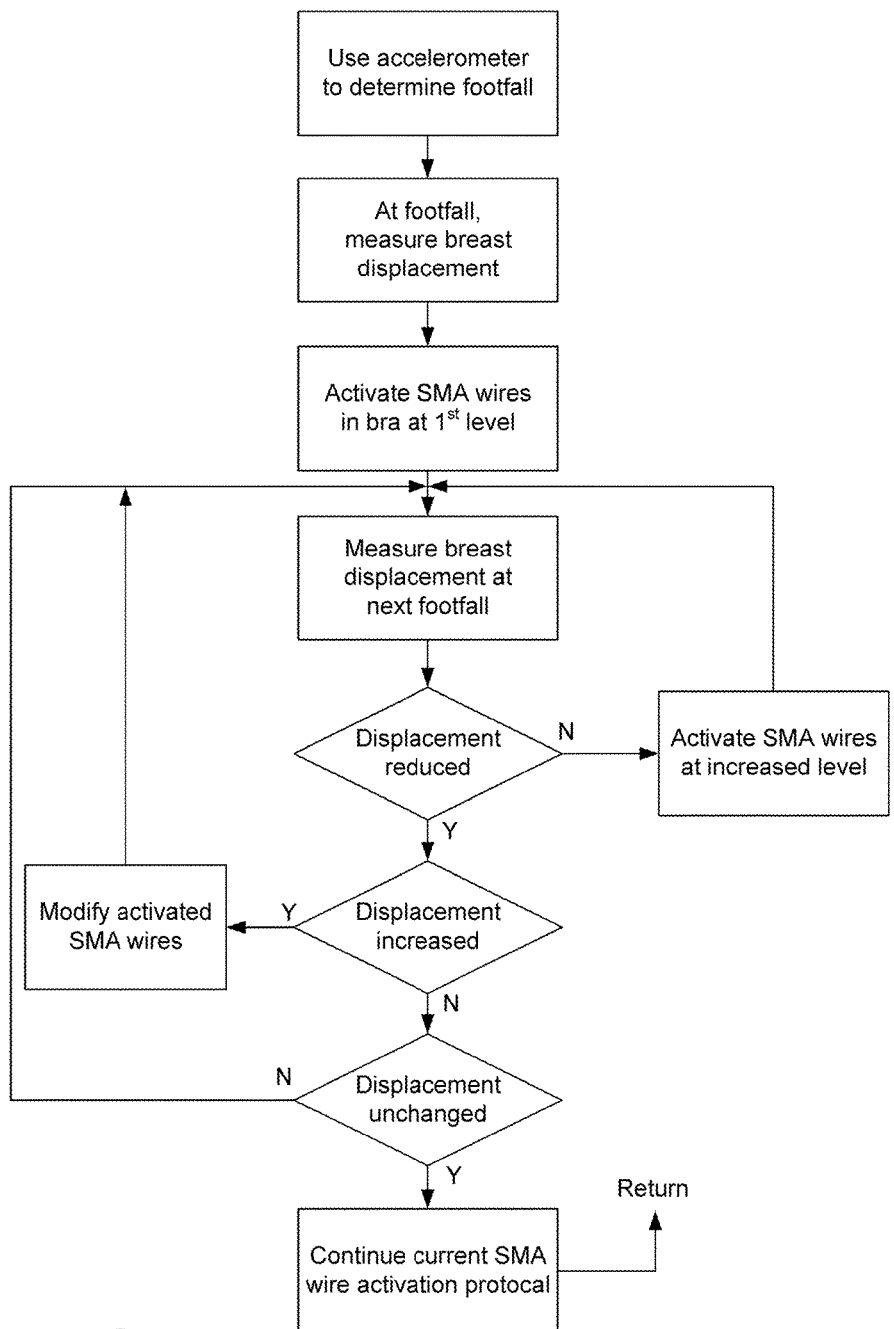
FIG. 5 is a flow chart of an algorithm executed by a microprocessor of the controller for the bra shown in FIG. 1

FIG. 4 is a rough mechanical representation of the dynamics of the active suspension system integrated into a bra of the present disclosure. A two pound weight, representing the mass of a breast, is suspended from a 24" length of 0.008" diameter super-elastic Nitinol wire that is formed into a U-shape. The wire is supported on a base to which is applied a disturbing force. An accelerometer mounted to the base senses the direction and magnitude of the disturbing force and selectively energizes and de-energizes the super-elastic wire so as to break the resonance of the disturbing force.

In the bra 10 of the present disclosure, an accelerometer 55 is mounted in or on the bra and is operable to provide multi-planar breast displacement data to the controller 50. The controller includes a power supply 51 that is small but capable of powering a microprocessor in the controller, the super-elastic Nitinol wires and the accelerometer. The controller 50 is preferably positioned at a location on the bra that will not itself bounce during movement of the wearer. Likewise, the accelerometer is positioned on the bra so that the acceleration vector detected by the accelerometer is only attributable to the movement of the wearer. Thus, in one embodiment, the electronics for the active suspension system of the bra 10 is mounted in one of the torso straps 14. The power supply 51 is preferably a rechargeable thin-film battery that can be recharged wireless, although other forms of power supply are contemplated.

The microprocessor of the controller receives the motion data from the accelerometer and uses that data to calculate the optimal timing and duration of current pulses from the power supply 51 to the super-elastic Nitinol wires 30, 31, 33 and 35 in a pattern that helps to minimize multi-planar breast displacement. The controller also measures breast displacement. This can be accomplished by accelerometers positioned at multiple locations on the bra cups 12, such as accelerometers 56, or by secondary tension wires that parallel the SMA wires 30, 31, 33, 35. The secondary tension wires can be SMA wires as well but calibrated so that stretching the wires under load produces a signal for the microprocessor. The microprocessor can be calibrated to relate a tension wire signal to a physical displacement of the breast. These same approaches to measuring actual breast displacement can be used in the embodiment described above for calibrated tightening of the bra to reduce breast movement.

For the active suspension feature of the bra 10, timing actuation patterns are based on software algorithms stored in the microprocessor. The microprocessor implements code that performs an algorithm which starts by capturing real time footfall vs. breast displacement data. The footfall data is generated by the accelerometer 55 since each step of the wearer produces an acceleration of the wearer's body. Based on known calibration data the algorithm directs the microprocessor to apply stimulus to or activate the super-elastic Nitinol wires and then measure the result. If the result is a decrease in measured displacement of the breast, a further stimulus is applied either sooner or more aggressively on the next successive footfall (as determined by the accelerometer) and the result is captured. If the result is again reduced displacement of the breast, further stimulus is applied with successive footfalls until either no additional reduction is possible or the breast displacement increases. If at any time displacement increases, a different stimulus is applied until the stimulus achieving minimal displacement is found. If the gait changes, physical activity (motion) speed or intensity changes, the algorithm recalibrates and predicts the optimal stimulus to minimize breast displacement. The microprocessor learns and adapts to the optimal stimulus sequence for a user for a particular gait or movement pattern and can reach a state of least displacement faster upon calibrating and recalibrating the appropriate pattern for the particular user and their walking, running or movement patterns.

For example, the stimulus could be that the super-elastic Nitinol wire in the right over-shoulder strap provides a counter-force on the top of the right bra cup. Simultaneously or alternatively, the stimulus could be that the super-elastic Nitinol wire in the left over-shoulder strap provides a counter-force on the top of the left bra cup. Similarly, the stimulus could be from the right underwire or left underwire or base of the bra, or from the top strap array. The stimulus could be from any additional straps and material added to the bra to achieve support and minimize breast displacement.

It can be appreciated that the protocol implemented by the controller can activate and deactivate the super-elastic Nitinol wire very rapidly even within a single footfall. Certain super-elastic Nitinol wires can be fully actuated in about ⅓ second. The SMA wire can be pulsed to achieve an increasing compression within a particular portion or strap of the bra. Activating the super-elastic Nitinol wires in the upper strap arrangement, such as wires 35 in straps 20 can reduce upward displacement of the breast, while activating super-elastic Nitinol wires 33 the shoulder straps 19 or the super-elastic Nitinol wire 30 in the bra underwire 13 can reduce downward displacement of the breast. Of course, when the breast is displaced downward there is no need for compression at the upper portion of the bra. Thus, the super-elastic Nitinol wires 35 can be deactivated when downward breast displacement is sensed, and likewise for the shoulder strap and underwire super-elastic Nitinol wires when upward displacement is sensed. The controller continuously cycles the activation and deactivation of the super-elastic Nitinol wires based upon when a footfall is sensed by the accelerometer. For instance, when the jolt of a footfall is sensed the breasts would ordinarily displace downward, so the super-elastic Nitinol wires 30 and 33 would be activated. As the athlete elevates the breast tend to displace upward, so the upper super-elastic Nitinol wires 35 can be activated while the lower wires are deactivated. Once the controller "learns" the wearer's gait the array of wires are activated and deactivated at precisely the right time to minimize overall breast displacement. The controller is constantly monitoring breast displacement and footfall so that any disruption in the pattern is accounted for as the controller "learns" the new movement pattern.

The controller 50, power supply 51 and accelerometer 55 can be removably mounted within the bra so that the electronic components can be removed during laundering. The SMA wires 30, 31, 33, 35 are preferably disposed within the protective tube 42 and embedded within the fabric of the bra, so the wires are protected during laundering.

In the illustrated embodiments, the SMA or super-elastic wires are formed of Nitinol which has a favorable response and recovery time. However, some shape memory or super-elastic materials do not recover (i.e., return to their original length after shortening) fast enough to be cycled at desirable intervals to account for and counteract breast movement. In this case multiple strands of SMA or super-elastic wire can be incorporated into the bra and the software protocol implemented by the controller can be modified such that at the first footfall a first SMA or super-elastic wire is activated. While the first wire is recovering, a second footfall occurs and a second SMA or super-elastic wire is activated. While the first and second wires are recovering, a third footfall occurs and a third wire is activated. By the time the fourth footfall occurs, the first wire has fully recovered and is ready to be activated again. This cycle is repeated over the four footfall cycle.

Wire cooling is critical to achieving the cycle speeds necessary to keep up with the movement of the breast during exercise. The fastest Olympic sprinters take at most four steps per second, a casual jog can be at two steps per second. The breast on the side of the footfall moves more in the Z (up/down) direction than the opposite breast, but both need dampening at each footfall. Thus, in order to be able to control or dampen breast displacement the Nitinol needs to be able to be stretched, dampen (either through the creation of stress induced Martensitic state or through Joule heating initiated dampening) and return to its initial length at a rate of 2 Hz if it is to be effective for jogging. The transition between Austenitic state and stress induced Martensitic state is instantaneous and reversible for SMA and super-elastic wires. Thus, if enough dampening is provided by this transition, such as for smaller breasts (B cup or smaller) with less mass movement to dampen) Joule heating is unnecessary. For breasts with larger mass (C cup or larger) it becomes necessary to use Joule heating to slow and reverse the transition from Austenite to stress-induced Martensite to provide additional dampening and control.

Cooling becomes critical as control using Joule heating becomes more aggressive. At its most aggressive, cooling can be accomplished by housing the Nitinol in an ethylene glycol and water filled tube. It can be further achieved through the use of silicone coating and silicone impregnated with diamond dust and finning to reject heat by-product as fast as possible into the air, reducing the heat conveyed to the wearer. Thus, in certain embodiments, the tube 42 can be silicone coated and/or filled with an ethylene glycol/water mixture In the illustrated embodiment, the accelerometer 55 is associated with the controller 50 and mounted in the bra 10. Alternatively, one or more accelerometers can be incorporated into or mounted to the shoe. In this embodiment, the accelerometers are configured to wirelessly transmit acceleration data to the controller 50, which means that the controller includes wireless capability such as Bluetooth. Since the accelerometers are measuring impact at footfall, they can be located at other positions on the wearer's body.

In the illustrated embodiment, the accelerometer(s) is/are measuring instantaneous acceleration as the foot of the wearer strikes a surface, whether by running or jumping. With each footfall the body experiences a jolt or acceleration spike, and it is this jolt coupled with the inertia of the breast mass that results in the breast displacement. However, other physical activities that do not necessarily involve a footfall can generate breast displacement. An accelerometer positioned in or immediately adjacent the bra will accurately measure the accelerations attributable to the physical activity. For instance, rowing involves significant movement of the upper body that can produce breast movement. For that matter, a wearer may be a passenger in a vehicle that is undergoing significant jolt, such as mounting biking. Again, the accelerometer can measure the instantaneous accelerations or jolt and provide immediate response to minimize breast displacement. For activities that do not involve a generally rhythmic pattern, such as mountain biking, the active suspension provided by the super-elastic shape memory material is less desirable. However, for activities that involve generally rhythmic movement, such as running or rowing, the super-elastic wire is appropriate.

The present disclosure should be considered as illustrative and not restrictive in character. It is understood that only certain embodiments have been presented and that all changes, modifications and further applications that come within the spirit of the disclosure are desired to be protected.

What is claimed is:

1. A bra for a wearer having breasts, shoulders a chest and a torso, the bra comprising:
   a pair of cups, each configured to receive the breasts of the wearer;
   a torso strap arrangement connected to the cups and configured to encircle the torso of the wearer to hold the pair of cups in position on the wearer's breasts;

a pair of shoulder straps connected between the cups and the torso strap and each configured to be seated on the shoulder of the wearer when the breasts are positioned in the pair of cups;

an array of straps extending from an upper portion of the cups to the each of the pair of shoulder straps across the chest of the wearer when the breasts are positioned in the pair of cups;

at least one shape memory wire integrated into at least each of said pair of shoulder straps;

an accelerometer associated with the bra operable to generate data indicative of instantaneous accelerations of the wearer that can induce breast displacement; and a controller electrically connected to the at least one shape memory wire and the accelerometer, the controller including an electrical power supply for providing electrical power to the shape memory wires, the controller including a processor operable to execute instructions for selectively providing electrical power to selected ones of the shape memory wires in response to data received from said accelerometer.

2. The bra of claim 1, further comprising at least one further shape memory wire integrated into and extending along a lower portion of each of the pair of cups and connected to said controller.

3. The bra of claim 2, wherein the at least one further shape memory wire is integrated into and further extends along a lower portion of the torso strap arrangement.

4. The bra of claim 1, further comprising at least one further shape memory wire integrated into and extending along an upper portion of the torso strap arrangement.

5. The bra of claim 1, wherein:
said array of straps includes at least one strap connected to an upper portion of each of said pair of cups and connected to a corresponding one of said pair of shoulder straps; and
said at least one strap at each of said pair of cups includes at least one shape memory wire integrated therein and extending from the cup to the shoulder strap, said at least shape memory wire connected to and controlled by said controller.

6. The bra of claim 1, wherein:
said array of straps includes at least two straps connected to an upper portion of each of said pair of cups and connected to a corresponding one of said pair of shoulder straps; and
said at least two straps at each of said pair of cups each include at least one shape memory wire integrated therein and extending from the cup to the shoulder strap, the shape memory wire connected to and controlled by said controller.

7. The bra of claim 1, further comprising a component for measuring the displacement of each breast within a corresponding one of said pair of cups, said component connected to said controller to provide displacement data to said controller, wherein said processor in said controller is operable to execute instructions for selectively providing electrical power to selected ones of the shape memory wires in response to data received from said accelerometer and to said displacement data.

8. The bra of claim 7, wherein the processor is operable to execute instructions to:
provide electrical power to selected ones of the shape memory wires;
receive new displacement data from said component for measuring the displacement; and
determine if the breast displacement has reduced, and if not then increasing the electrical power provided to selected ones of the shape memory wires.

9. The bra of claim 8, wherein the processor is operable to execute instructions to evaluate whether the breast displacement has reduced below a threshold and if so continuing to cycle the electrical power to the shape memory wires to maintain the breast displacement.

10. The bra of claim 1, wherein the shape memory wire is Nitinol.

11. The bra of claim 10, wherein the shape memory wire is super-elastic Nitinol.

12. The bra of claim 1, wherein the shape memory wire is contained within a tube.

13. The bra of claim 12, wherein the tube includes at least one of an ethylene glycol-water mixture within tube and a silicone coating.

14. The bra of claim 1, wherein the accelerometer is mounted in the bra.

15. The bra of claim 1, wherein:
the accelerometer is separate from the bra, and
the accelerometer and said controller are capable of wireless communication of said data from said accelerometer to said controller.

* * * * *